United States Patent [19]

Inoue et al.

[11] Patent Number: Plant 7,339

[45] Date of Patent: Sep. 25, 1990

[54] SHIITAKE MUSHROOM PLANT NAMED 'HOKKEN 601'

[75] Inventors: Sadayuki Inoue, Mibu; Sumio Ayusawa, Utsunomiya, both of Japan

[73] Assignee: Hokken Sangyo Co., Ltd., Tochigi, Japan

[21] Appl. No.: 217,564

[22] Filed: Jul. 18, 1988

[30] Foreign Application Priority Data

Jul. 20, 1987 [JP] Japan ..... 2384

[51] Int. Cl.[5] ..... A01H 15/00

[52] U.S. Cl. ..... Plt./89

[58] Field of Search ..... Plt./89

[56] References Cited

U.S. PATENT DOCUMENTS

| | | | |
|---|---|---|---|
| P.P. 2,050 | 4/1961 | Robbins | Plt. 89 |
| P.P. 4,759 | 8/1981 | Pollock | Plt. 89 |
| P.P. 5,772 | 7/1986 | Royse et al. | Plt. 89 |
| P.P. 5,773 | 7/1986 | Royse et al. | Plt. 89 |

FOREIGN PATENT DOCUMENTS 58-48299 3/1983 Japan ..... 47/1.1

OTHER PUBLICATIONS

Rinaldi, A., et al., "*Tricholomopsis edodes*" *The Complete Book of Mushrooms,* Crown Publishers, Inc., N.Y., 1974, p. 176..

Chang, S. T., et al., "1.2 *Lentinus edodes*"; G. Lentinus edodes, 22 Cultivation of Lentinus edodes, *The Biology and Cultivation of Edible Mushrooms,* Acedemic Press, N.Y., 1978, pp. 31, 32, 104–106 and 461–473.

*Primary Examiner*—James R. Feyrer

*Attorney, Agent, or Firm*—Morgan & Finnegan

[57] ABSTRACT

The present invention relates to a new and distinct horticultural variety of shiitake mushroom, Lentinus edodes (Berk.) Sing. This new variety, named "Hokken 601", was discovered by crossbreeding. It is adaptable to short term cultivation in sawdust beds and is characterized by rapid growth in these beds. "Hokken 601" offers superior yields and firmer flesh than other varieties of shiitake.

12 Drawing Sheets

BACKGROUND OF THE INVENTION

Shittake mushrooms, Lentinus edodes (Berk.) Sing., grow naturally on the dead wood of many hardwood species. In Japan, shiitake mushrooms have been cultivated on bed logs for 300 years, and today their cultivation is an important agricultural business. In 1988, 83,000 tons of fresh shiitake mushrooms and 12,000 tons of dried shittake mushrooms were produced. Because most shiitake mushrooms have been cultivated on logs, many commercial varieties have been bred for log cultivation.

Sawdust bed cultivation of shiitake mushrooms was begun about twenty years ago, and the same varieties adaptable to log cultivation have been used in sawdust bed cultivation as well. Log cultivation is long term, while sawdust bed cultivation is short term. Because sawdust bed cultivation is short term, it is a better method for commercial and mass production, but varieties of shiitake suitable for sawdust bed cultivation are limited. The common commercial varieties used for log cultivation bear normal fruit bodies on logs after six to eighteen months incubation. If these common varieties are incubated on sawdust beds less than three months, either the fruit bodies do not develop, or abnormal fruit bodies without caps appear at the flush time. However, when these common varieties are incubated for four to six months, normal fruit bodies appear.

In 1985 the breeder developed "Hokken 600" (registration No. 1791 based on the Japanese seed and Seedlings Law), which is suited for sawdust bed cultivation. "Hokken 600" bears normal fruit bodies after only three months incubation at 20° C. under general commercial conditions.

The object of this breeding was to select a variety of shiitake adaptble to sawdust cultivation. The breeding process is described below. This breeding project was carried out from 1981 to 1987 at the Edible Mushroom Institute, Hokken Sangyou Co., Ltd., in Mibu-machi, Shimotsuga-gun, Tochigi-ken, Japan.

1. One parent is "HL7722", a tissue culture strain isolated from "Hokken 58", commonly used for commercial cultivation. The other parent is "HL7951", a wild strain. Monokaryon mycelia were isolated from fruit bodies of each parent.

2. Dikaryon mycelia were produced by crossing monokaryon mycelia.

3. These dikrayon mycelia were selected first on the basis of the degree of mycelial growth on PDA-media in the laboratory of the Edible Mushroom Institute, Hokken Sangyou Co., Ltd.

4. The second selection of the dikaryon mycelia was done on the basis of the mycelial covering days on sawdust media in bottles in the same laboratory.

5. The selected dikaryon mycelia were cultivated twice on sawdust beds at the green house of the Edible Mushroom Institute, Hokken Sangyou Co., Ltd., for one year. Finally, this new variety of shiitake mushroom was selected by evaluating the desirable cultivation characteristics.

6. At the same time, the selected dikaryon mycelia was cultivated on logs at the laying yard of the Edible Mushroom Institute, Hokken Sangyou Co., Ltd., for two years, and this shiitake mushroom proved adaptable to log cultivation as well.

This shiitake mushroom was cultured in contrast with thirty one types of commercially cultivated mushrooms, including the parent types, on PDA-media. The results showed that this shiitake mushroom formed lines of antagonism, or zone lines, between all types, and proved to have genetic sex factors different from all thirty one types.

Sawdust bed cultivation was done under the following conditions to study the properties of this shiitake mushroom. Incubation was done at 20° C. temperature for 90 days, and break or flush was done at 15° C. temperature in 70% to 90% humidity for 90 days. Bag cutting was used for the first flush or break treatment, and water submergence for the second and third treatments. Normal fruit bodies were not observed on the two parent varieties after 90 days of incubation. "Hokken 600", a variety for sawdust bed cultivation, was used as a control variety. Change of yield at first, second and third flush is shown in FIG. 4. This shiitake mushroom yielded 358 grams of fruit bodies per bag of 1.2 kg sawdust bed and was confirmed to be suitable for sawdust bed cultivation. The number of days required between the break treatment and the flush peak of this shiitake mushroom is ten days, and notably shorter than that of "Hokken 600" by twelve days.

This shiitake mushroom is asexually reproduced by periodic transfer of its dikaryon mycelium. Subculture is a common method for maintaining mushroom cultures on suitable media. Media such as PDA (potato dextrose agar) or MEA (malt extract agar) are used as shiitake culture ground, and are subcultured every one to six months. To produce spawn, cut pieces of dikaryon mycelia grown on PDA or MEA are inoculated in sawdust or wood media, and the inoculated media is incubated at 20° C. for one to three months. Sawdust spawn is used on sawdust beds, and sawdust or wood spawn are used on logs in commercial cultivation.

SUMMARY OF THE INVENTION

The outstanding characteristics of this shiitake mushroom are its shorter incubation period within three months on sawdust beds than standard shiitake mushroom varieties, its quicker flush peak after break treatment, and its increased yield per bag of sawdust bed as compared with the yield of the standard shiitake mushrooms.

BRIEF DESCRIPTION OF THE ILLUSTRATIONS

FIGS. 8, 9 and 10 show the first flush of this shiitake mushroom on sawdust beds in plastic bags.

FIG. 9 is an enlarged view of FIG. 8.

FIG. 10 is an enlarged view of FIG. 9.

BOTANICAL DESCRIPTION

Figure 1:
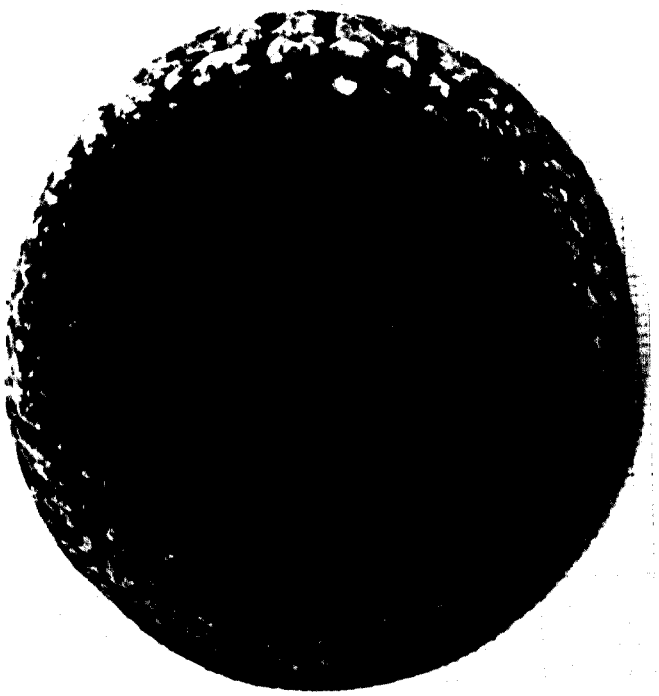
FIG. 1 shows a top view of the fruit body of the shiitake mushroom of the present invention.
Figure 2:
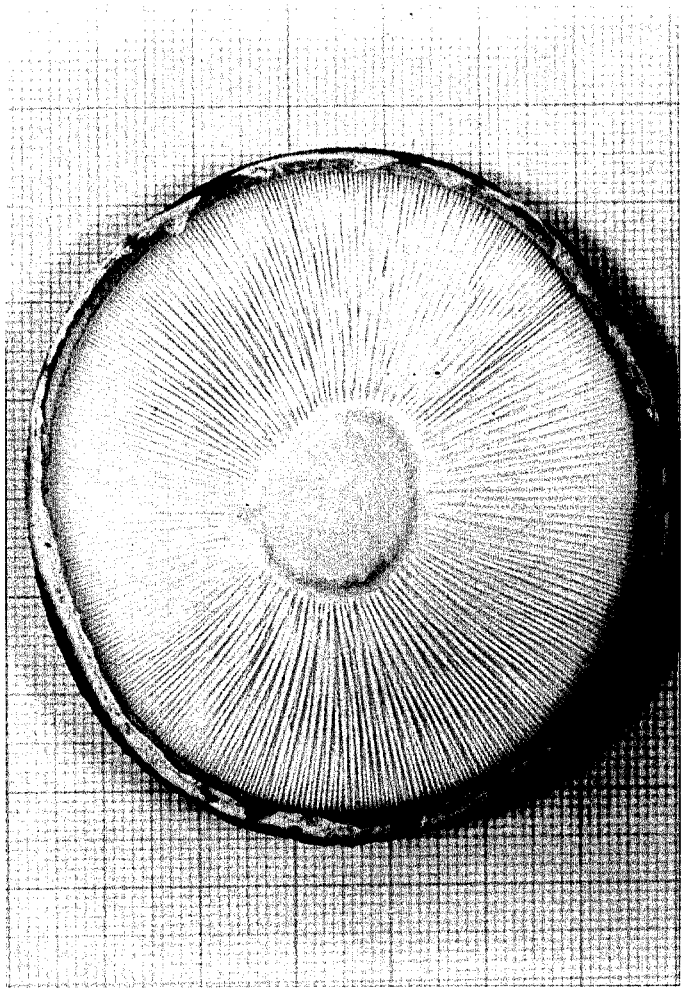
FIG. 2 is a bottom view of the fruit body of the shiitake plant of the present invention.
Figure 3:
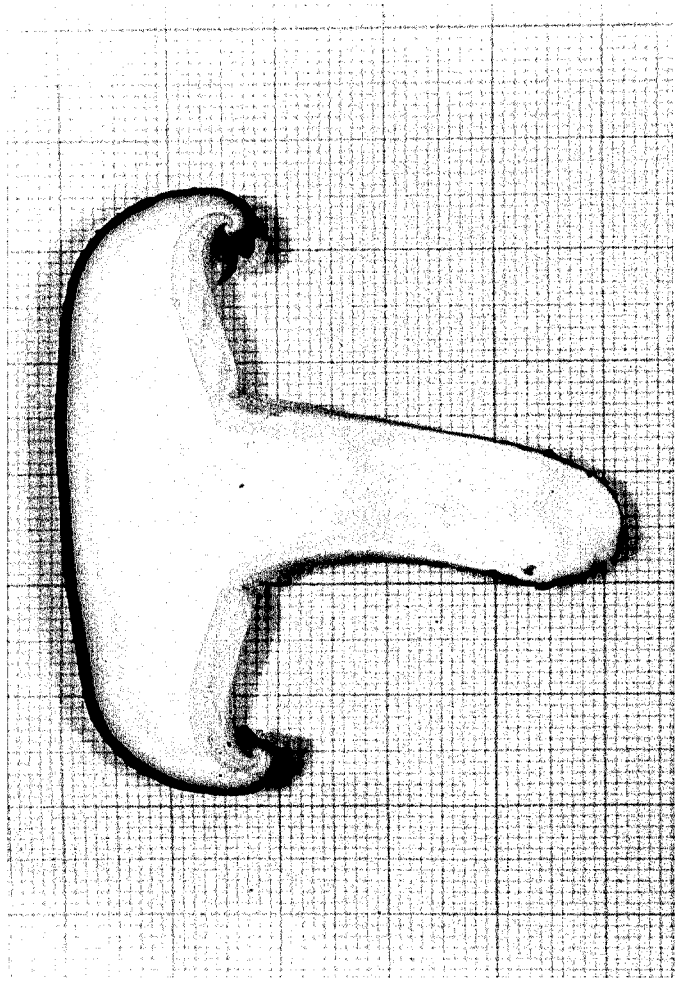
FIG. 3 is a side view of the fruit body of the shiitake plant of the present invention.
Figure 4:
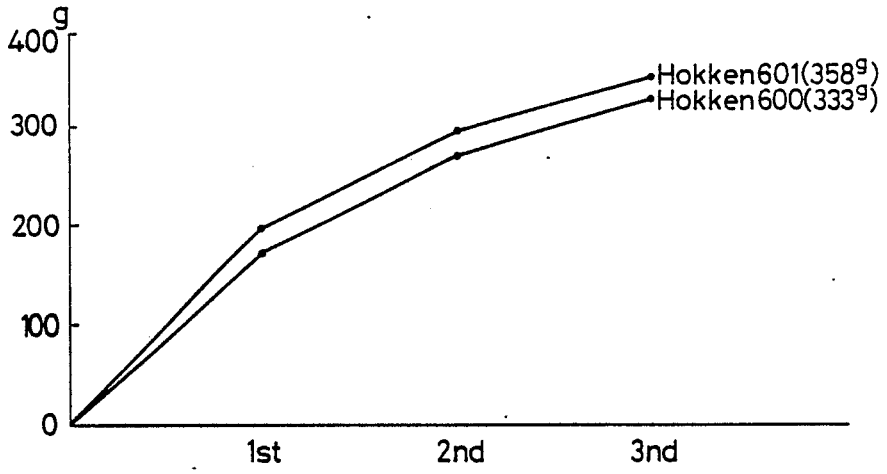
FIG. 4 illustrates the results of comparative examination of the shiitake plant of the present invention, "Hokken 601," in sawdust bed cultivation. "Hokken 600" was used as the control variety.
Figure 5:
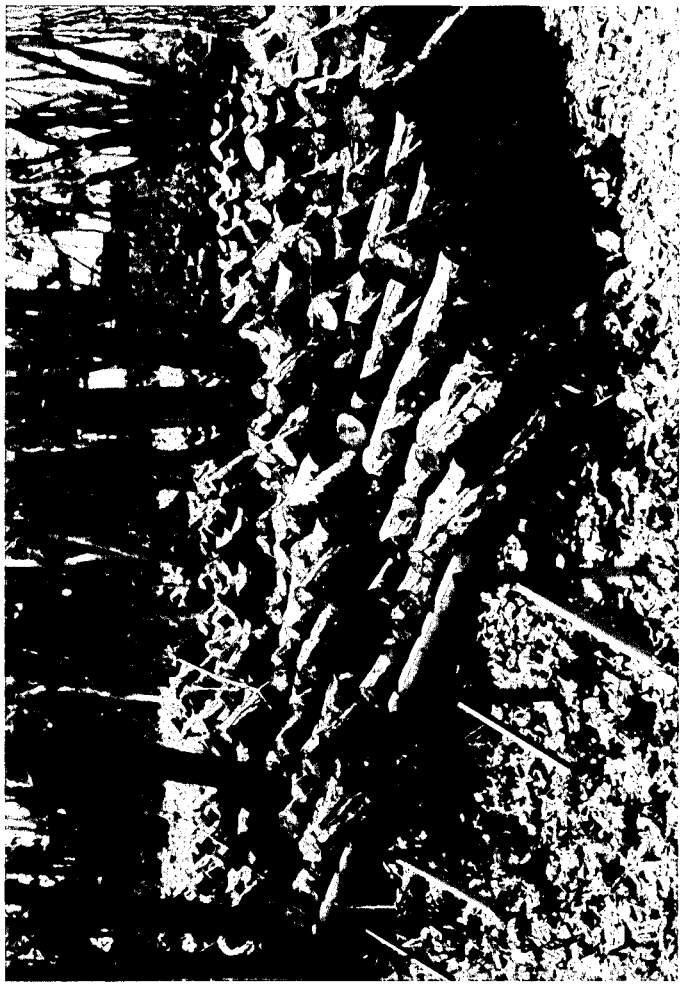
FIG. 5 shows the placement of logs in the laying yard.
Figure 6:
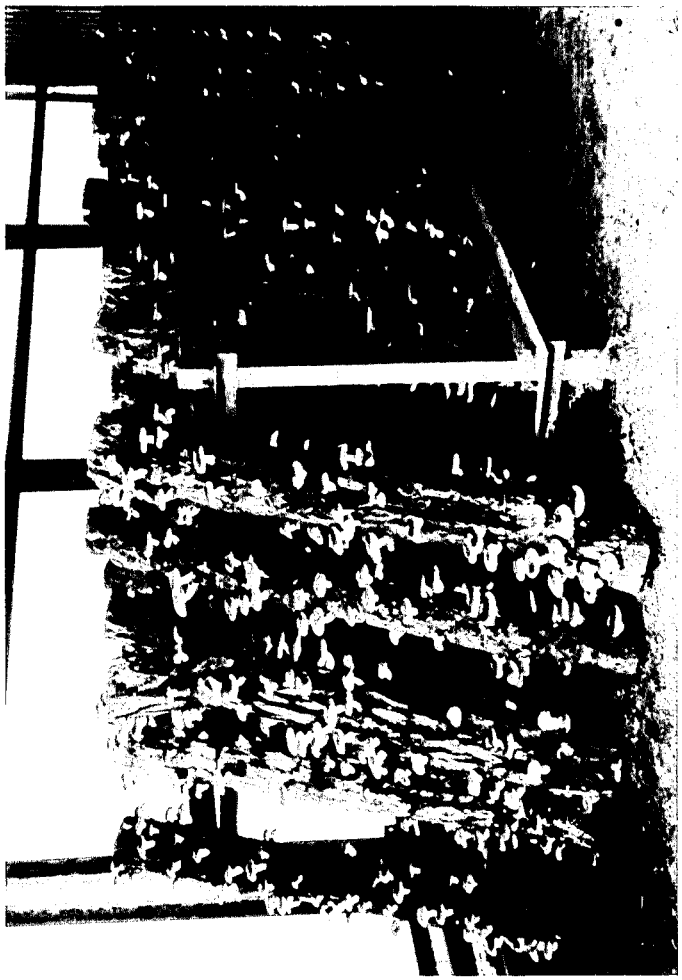
FIGS. 6 and 7 show the first flush of this shiitake mushroom on bed logs in the experimental laying yard.
Figure 7:
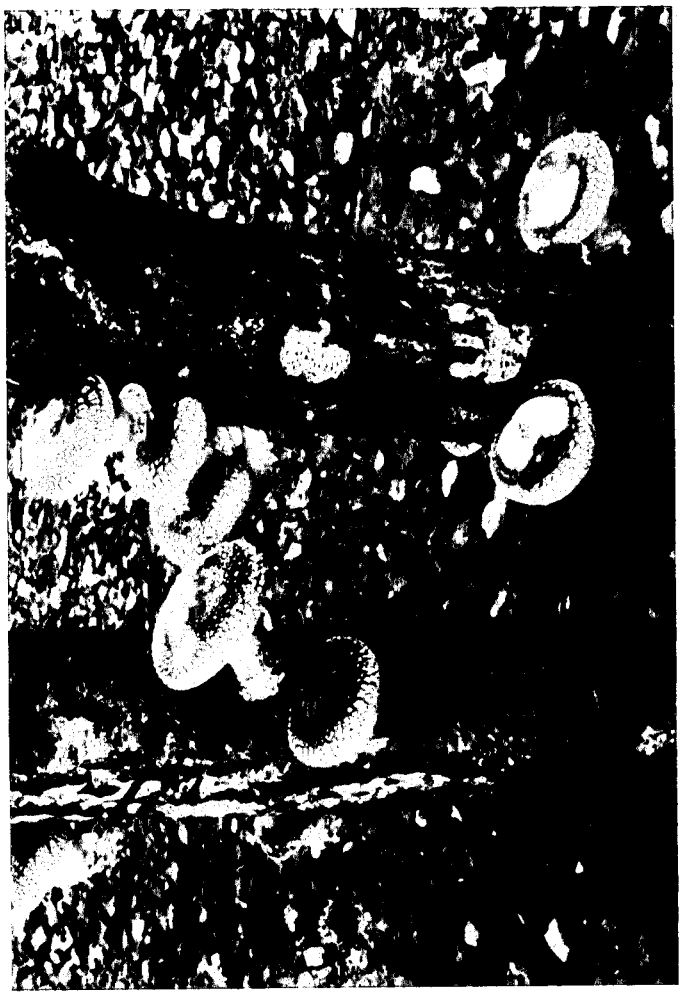
Figure 9:
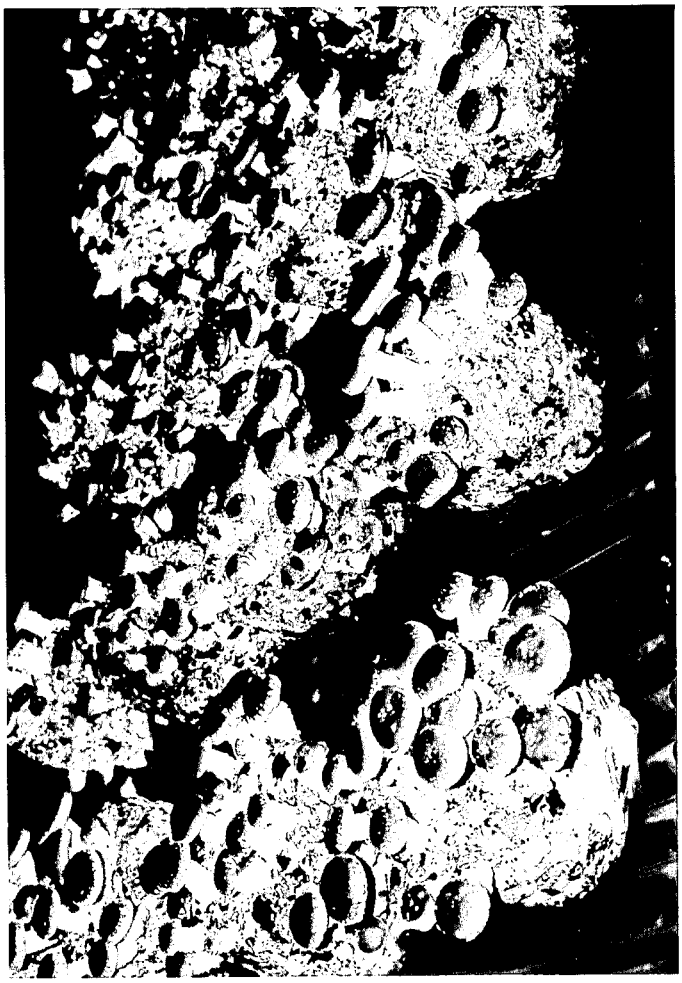
Figure 10:
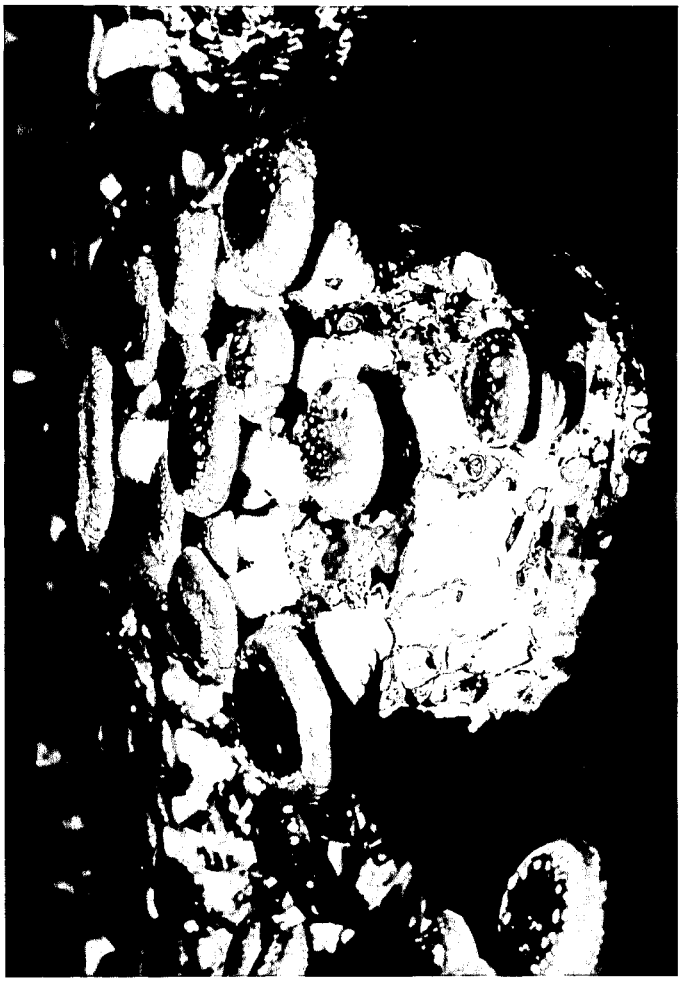
Figure 11:
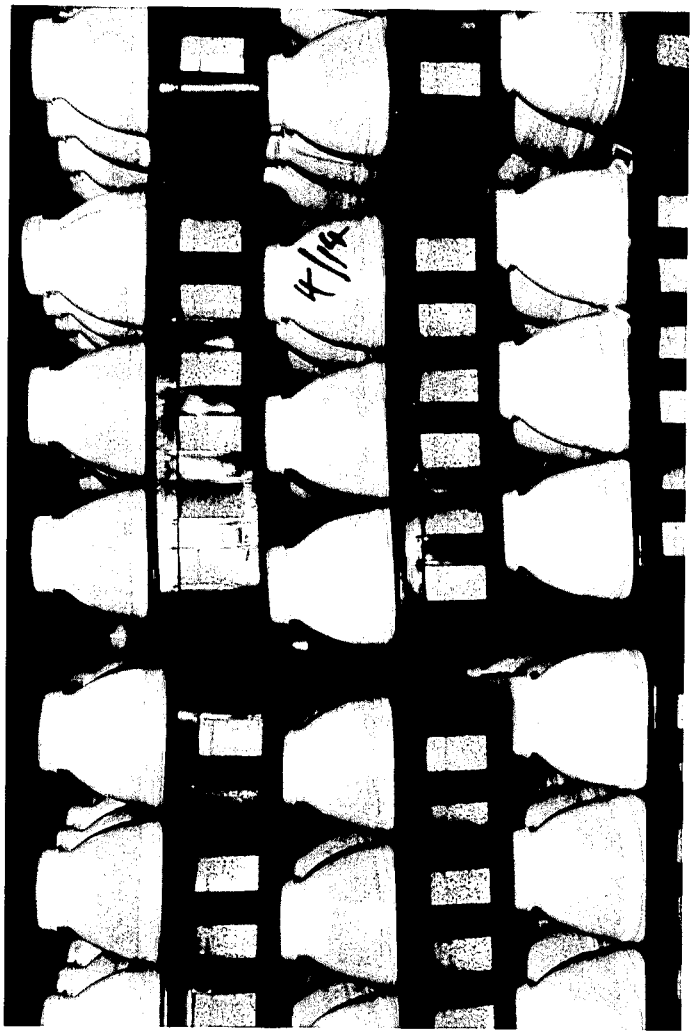
FIG. 11 shows the state of incubation of this shiitake mushroom on sawdust beds in bottles.
Figure 12:
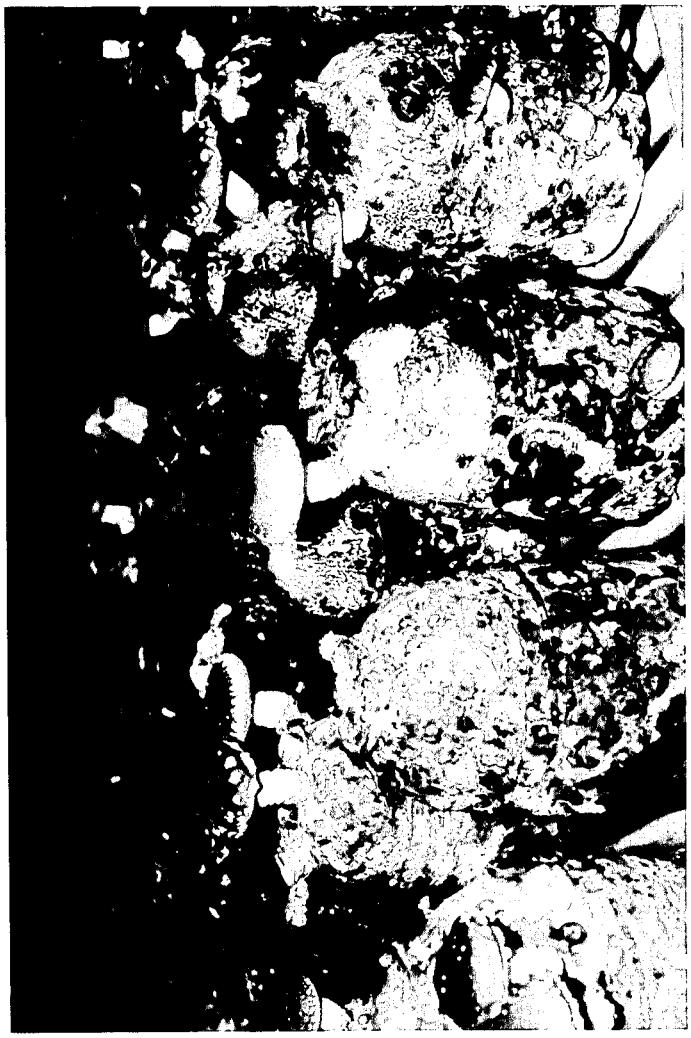
FIG. 12 shows the state of the first flush after incubation.

The following detailed description of the shiitake mushroom of the present invention is given with reference to the Muncell Book of Color 1976, and the Japanese standards of judgment for shiitake mushrooms. This description is of a shiitake mushroom grown under commercial conditions. When this shiitake mushroom is grown under different conditions, it will be obvious that its appearance may be different than that described.

The cap or pileus of this shiitake mushroom is of generally convex shape when immature and changes to become nearly plane when mature. Cap diameter of the mature fruit body varies between approximately 44 mm and 77 mm, with an average of 56 mm, which is relatively smaller than the standard type. The color of the cap is between 7.5YR 6/6 and 7/6. The flesh of the cap is 6 to 14 mm in thickness, averaging 11 mm, which is the average thickness of the standard type. The flesh texture is also the same as the standard type.

Scales cover the entire surface of the cap, expecially concentrating around the outer edges. The scale color is between 7.5YR 9/2 and 6/4.

The arrangement of gills or lamellae is normal. The gill width is 2 to 5 mm, with an average of 4 mm, slightly narrower than the standard type. The gill is generally equal to color 10 YR 9/1.

The length of the stem or stipe is between 33 mm and 60 mm, with an average of 44 mm, about the same as the standard type. The stem thickness is between 7 mm and 15 mm, the average being 11 mm, which is also roughly the same as the standard type. The color of the stem is between 10YR 9/1 and 9/2. The stem without a volva, is covered with same colored follicles.

The ratio between the cap diameter and the stem length is 1.0 to 1.8, the average being 1.3.

The spore print color is the equivalent of 10YR 9/1.

We claim:

1. A new and distinct variety of shiitake mushroom substantially as shown and described.

* * * * *

MISSING PAGE TEMPORARY NOTICE

PATENT # PP7339 FOR ISSUE DATE 9-25-1990

HAS BEEN SCANNED, BUT WITH MISSING PAGE(S). UPON RECEIVING OF MISSING PAGE(S), THE ENTIRE DOCUMENT WILL RE RESCANNED. PLEASE CALL IMAGE DATA ADMINISTRATION STAFF OF 557-6154 IF YOU HAVE A QUESTION. ASK FOR DAVE GROOMS, ANITA YOUNG OR POLA JONES.

THIS NOTICE IS FOR THE MISSING PAGE CONTAINING:

DRAWING SHEET # 8